Examiner

Reissued Dec. 24, 1935

Re. 19,794
1,773,611

UNITED STATES PATENT OFFICE 19,794

PREPARATION OF ACETYLENE

Martin Banck, Bucharest, Rumania, assignor to Ruhrchemie Aktiengesellschaft, Oberhausen-Holten, Germany, a corporation of Germany No Drawing. Original No. 1,773,611, dated August 19, 1930, Serial No. 172,561, March 3, 1927. Application for reissue August 5, 1932, Serial No. 627,601, and in Germany March 15, 1926

3 Claims. (Cl. 260—170)

This invention relates to the art of treating methane and other hydrocarbons for the preparation of acetylene and hydrogen.

According to certain prior processes, methane gas has been heated to high temperatures for the production of lamp black or soot, in which processes the methane is said to be completely decomposed into carbon and hydrogen. The heating has thus split up the methane into its elemental components. If any intermediate products are formed, they are apparently decomposed before leaving the furnace.

It has also been reported in the literature that, upon the heating of hydrocarbons, such as methane, acetylene is first formed but that at higher temperatures this splits up directly into carbon and hydrogen; see, for example, Prof. Lewes' article in Proc. Royal Soc. London, 55, 91–107 (1894). This article states that the acetylene first formed polymerizes to form benzene, etc. at relatively low temperatures but that it "decomposes at about 1200° C. with liberation of carbon", indicating that at temperatures much above this decomposition point it is impossible to obtain any substantial yields of acetylene. I have found, on the contrary, that much larger yields of acetylene can be obtained at higher temperatures by exhausting the reaction products from the reaction zone or by preventing dissociation of the acetylene by diluting the reaction gases with other inert gases. By these means a subatmospheric pressure of methane is obtained in the reaction zone.

I have established by systematic experiments that the yield from the well known reaction:

$$2CH_4 \rightleftarrows C_2H_2 + 3H_2 \quad (1)$$

depends on the contact between the quantity of methane and the surface heated to temperatures higher than the temperature for total dissociation of methane, i. e., for practical purposes, between 1400° and 2000° C.

The yield from this reaction of methane into acetylene and hydrogen increases and approximates more closely the theoretical yield in proportion to the extent of the surface of contact.

In other words, it is dependent on the extent to which the whole of the gas is brought into contact with the surfaces heated to the temperatures necessary for the reaction.

The process is carried out in the main by passing the gas, either preheated or not, through an electric furnace with carbon electrodes. In order to get a greater contact surface the interior of the furnace is filled with pieces of carbon irregularly broken up, or of some uniform shape but of different sizes. In an electric furnace with electrodes of carbon fragments I obtained a yield of about 70% of acetylene (exactly 68.8%).

I have further found that the yield in the transformation of methane into acetylene can be increased if one uses as resistances in the electric furnace any variety of carbon or material which contains carbon and is good conductor of electricity, or any other material which has a large contact surface and is made an electrical conductor by one of the known means and is raised to and kept at the temperatures necessary for the reaction, i. e. temperatures higher than 1400° C.

I have also found that one can use in the furnace as contact mass, any porous material which can withstand the temperatures mentioned above, at which the reaction (1) takes place. This material may, or may not be a conductor of electricity.

By varying the resistance in the electric furnace, the consumption of almost 1 kw/hr. which had been found necessary for the transformation of a cubic meter of methane, can be reduced to about ½ kw/hr., for the same quantity.

I have noticed and determined experimentally that to increase and maintain the contact surface at the necessary reaction temperatures one can employ other electric furnaces, or other means of heating without resistances.

I have found that it is possible to employ for the same purpose, and with the same result, an arc furnace with the arc expanded by a magnetic field or by a strong current of gas.

In all cases one must pay scrupulous attention to the tightness of the apparatus so as to prevent any access of air. It is also absolutely necessary to prevent the diffusion of hydrogen which is necessary for maintaining the stability of the acetylene at temperatures lower than the temperatures of formation of this hydrocarbon.

By experience I have found that the following things are advantageous to assure the greatest yield from this reaction and to keep the furnace in continuous operation:

1. The gases should be preheated.

2. The heated gases should flow into the furnace directly into a zone higher in temperature than 1400° C.

3. A reduced pressure produced by an exhauster should be maintained in the furnace to help the transformation of methane into acetylene and hydrogen i. e. to increase the yield.

Further I have found that to obtain acetylene one is not obliged to prepare it only from methane. One can obtain it from all other gaseous or gasified hydrocarbons, mixtures of natural or synthetic hydrocarbons, and in general from any other organic material under the condition that it should first pass through the methane phase, with or without the addition of hydrogen.

I have shown by experiments that one condition which assists the transformation reaction of methane by preventing the dissociation of a part of the acetylene (i. e. by increasing its thermic stability) is to dilute these gases with other inert gases under the conditions under which the reaction takes place.

I claim:—

1. In the manufacture of acetylene, the process which comprises passing a gas, selected from a class consisting of methane and gases containing a substantial quantity of methane, into a reaction zone, maintained at temperatures ranging from about 1400° C. to 2000° C. and in the absence of air, and exhausting the acetylene-containing reaction products from the reaction zone thereby producing a reduced pressure in said zone.

2. The process of claim 1 wherein the gas employed comprises methane diluted with an inert gas.

3. The process of claim 1 wherein the gas employed is diluted with hydrogen.

MARTIN BANCK.